(12) United States Patent
Wehnes et al.

(10) Patent No.: US 8,540,981 B1
(45) Date of Patent: Sep. 24, 2013

(54) BACILLUS STRAINS USEFUL AGAINST CALF PATHOGENS AND SCOURS

(75) Inventors: Christopher A. Wehnes, Waukesha, WI (US); Keith J. Mertz, Neosho, WI (US); Mari Ellen Davis, Waukesha, WI (US); Alexandra Helena Smith, Greendale, WI (US); Thomas G. Rehberger, Wauwatosa, WI (US)

(73) Assignee: DuPont Nutrition Biosciences ApS, Copenhagen (DK)

( * ) Notice: Subject to any disclaimer, the term of this patent is extended or adjusted under 35 U.S.C. 154(b) by 969 days.

(21) Appl. No.: 12/498,734

(22) Filed: Jul. 7, 2009

Related U.S. Application Data

(60) Provisional application No. 61/078,708, filed on Jul. 7, 2008.

(51) Int. Cl.
- *A01N 63/00* (2006.01)
- *A01N 65/00* (2009.01)
- *C12N 1/20* (2006.01)

(52) U.S. Cl.
USPC .............. 424/93.462; 424/93.1; 424/823; 435/252.5; 435/839

(58) Field of Classification Search
None
See application file for complete search history.

(56) References Cited

U.S. PATENT DOCUMENTS

| | | |
|---|---|---|
| 2,906,622 A | 9/1959 | Lewis |
| 2,942,977 A | 6/1960 | Lewis |
| 3,892,846 A | 7/1975 | Wortham |
| 4,820,531 A | 4/1989 | Tomes |
| 4,919,936 A | 4/1990 | Iwanami |
| 5,073,367 A | 12/1991 | Hguyen |
| 5,478,557 A | 12/1995 | Nisbet |
| 5,482,723 A | 1/1996 | Sasaki |
| 5,507,250 A | 4/1996 | Reddy |
| 5,540,924 A | 7/1996 | Onishi |
| 5,703,040 A | 12/1997 | Landolo |
| 5,718,894 A | 2/1998 | Mann |
| 5,830,993 A | 11/1998 | Biecha |
| 5,840,318 A | 11/1998 | Marshall |
| 5,879,719 A | 3/1999 | Valentine |
| 5,945,333 A | 8/1999 | Rehberger |
| 5,964,187 A | 10/1999 | Willis |
| 5,965,128 A | 10/1999 | Doyle |
| 6,008,195 A | 12/1999 | Selsted |
| 6,156,355 A | 12/2000 | Shields, Jr. |
| 6,207,411 B1 | 3/2001 | Ross |
| 6,221,650 B1 | 4/2001 | Rehberger |
| 6,346,422 B1 | 2/2002 | Butty |
| 6,410,016 B2 | 6/2002 | Maruta |
| 7,247,299 B2 | 7/2007 | Lin et al. |
| 7,384,628 B2 * | 6/2008 | Rehberger et al. ........... 424/93.4 |
| 7,618,640 B2 | 11/2009 | Rehberger et al. |
| 7,754,469 B2 | 7/2010 | Baltzley et al. |
| 2002/0018770 A1 | 2/2002 | Maruta |
| 2003/0099624 A1 | 5/2003 | Porubcan |
| 2004/0104175 A1 | 6/2004 | Rawson |
| 2004/0170617 A1 | 9/2004 | Finegold |
| 2005/0255092 A1 | 11/2005 | Rehberger |
| 2006/0067924 A1 | 3/2006 | Lee et al. |
| 2007/0202088 A1 | 8/2007 | Baltzley et al. |
| 2009/0275109 A1 | 11/2009 | Bellot et al. |
| 2009/0280090 A1 | 11/2009 | Rehberger |

FOREIGN PATENT DOCUMENTS

WO    2005112658    12/2005

OTHER PUBLICATIONS

Office Action mailed Mar. 11, 2010 for Canadian App. No. 2,566,617.
Teo et al., "Applied & Environmental Microbiology," (Aug. 2005) vol. 71, 8:4185-4190.
Timmerman, H. M. et al, "Health and growth of veal calves fed milk replacers with or without probiotics," J. Dairy Sci. (2005) 88:2154-2165.
Torrallardona, D. et al, "Effect of fishmeal replacement with spray-dried plasma and colistin on intestinal structure, intestinal microbiology, and performance of weanling pigs challenged with *Escherichia coli* K99," J. Anim. Sci. (2003) 81:1220-1226.
Van Dijk, A. et al, "Growth performance of weanling pigs fed spray-dried animal plasma: a review," Livestock Production Science (2001a) 68:263-274.
Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.
Vance, H. N., "A survey of the alimentary tract of cattle for *Clostridium perfringens*," Can. J. Comp. Med. Vet. Sci. (1967) 31:260-264.
"Watt Feed E-News Feb. 8, 2005" 'Online! Feb. 8, 2005, pp. 1-6, XP002342563, retrieved from the Internet: URL:http://www.wattnet.com/Newsletters/feed/htm/FEBFEED05.htm> [source: PCT/US05/017141 ISR].
Wattiau, P et al, "A PCR test to identify *Bacillus subtilis* and closely related species and its application to the monitoring of wastewater biotreatment," Appl Microbiol Biotechnol 56:816-819, 2001.
Wattiau et al, Appl. Microbiol Biotechnol 2001, vol. 56, p. 816-819.
Wiard, T et al, "The effect of a biological litter treatment on *Salmonella* prevalence in turkey breeder flock litter," Poultry Science 80:127 (Suppl. 1):1-4, 2001.
Casey, P. G. et al, "A five-strain probiotic combination reduces pathogen shedding and alleviates disease signs in pigs challenged with *Salmonella enterica* serovar Typhimurium," Appl. Environ. Microbiol, (2007) 73:1858-1863.
Wiard, T et al, Application of plating enumerations and denaturing gradient gel electrophoresis to study turkey poult gastrointestinal tract bacterial diversity, (4 pgs) presented at the Poultry Science Assoc meeting, Madison, WI 2003.
Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.

(Continued)

*Primary Examiner* — Debbie K Ware
(74) *Attorney, Agent, or Firm* — Whyte, Hirschboeck Dudek S.C.

(57) ABSTRACT

The present invention relates to a composition including *Bacillus subtilis* strains 3A-P4 ATCC Accession No. PTA-6506, 22C-P1 ATCC Accession No. PTA-6508, and LSSA01 NRRL Accession No. NRRL B-50104. The present invention also relates to a method of administering an effective amount of a composition comprising *Bacillus subtilis* strains 3A-P4 ATCC Accession No. PTA-6506, 22C-P1 ATCC Accession No. PTA-6508, and LSSA01 NRRL Accession No. NRRL B-50104 to a calf.

19 Claims, 1 Drawing Sheet

(56) References Cited

OTHER PUBLICATIONS

Williams, J. G. et al, "DNA polymorphisms amplified by arbitrary primers are useful as genetic markers," Nucleic Acids Res. (1990) 18:6531-6535.

Willoughby, D H et al, "Periodic recurrence of gangrenous dermatitis associated with Clostridium speticum in a broiler chicken operation," J Vet Diagn Invest 8:259-261, 1996.

Wills, "Escherichia coli postweaning diarrhea," Vet Clinics N Am, pp. 138-140, 2000.

Wilson, M, "Segregated early weaning," Pig Lett. (1995) 15:17-20.

Wistuba et al, "Influence of fish oil supplementation on growth and immune system characteristics of cattle," J. Anim. Sci. (2005) 83:1097-1101.

Wu, X. Y. et al, "Characterization of Mesophilic bacilli in feces of feedlot cattle," J. Appl. Microbiol. (2007) 102:872-879.

Yang, H. et al, "Effect of adding a Bacillus based direct fed microbial on performance of nursery pigs fed diets with or without antibiotics," J. Anim. Sci. (2003).

Yang, W., "Effects of direct-fed microbial supplementation on ruminal acidosis, digestibility, and bacterial protein synthesis in continuous culture," Animal Feed Science and Technology, (2004) 114(4): 179-193.

Zhu, X Y, "16S rRNA-based analysis of microbiota from the cecum of broiler chickens," Applied and Environmental Microbiology, 68(1):124-137, Jan. 2002.

Zoetendal, E G et al, Molecular ecological analysis of the gastrointestinal microbiota: a review, J of Nutrition pp. 465-472, 2004.

International Search Report and the Written Opinion of the International Searching Authority, or the Declaration mailed Dec. 9, 2005 for PCT/US2005/017141, filed on May 13, 2005.

International Search Report and the Written Opinion of the International Searching Authority, or the Declaration mailed Dec. 6, 2009 for PCT/US2009/40920, filed on 17/04/200.

Non-Final Office Action mailed May 13, 2009 for U.S. Appl. No. 11/565,474, filed Nov. 30, 2006.

Notice of Allowance, mailed Apr. 10, 2009 for U.S. Appl. No. 11/129,767, filed May 13, 2005.

Final Office Action mailed Jan. 22, 2009 for U.S. Appl. No. 11/129,767, filed May 13, 2005.

Non-Final Office Action mailed Feb. 5, 2008 for U.S. Appl. No. 11/129,767, filed May 13, 2005.

Sale: Agtech Products, Inc. purchased strain Bacillus subtilis 2084 from a third party. At least as early as Sep. 10, 2004.

Sale: Agtech Products, Inc. purchased strain Bacillus licheniformis 21 from a third party. At least as early as Jan. 30, 2007.

A multiple-strain product, commercially sold as Microsource direct-fed microbial, containing Bacillus strains Bacillus subtilis 27 (BS 27), Bacillus licheniformis (previously thought to be B. amyloliquefaciens) 842, and Bacillus licheniformis 21 (BI 21) has been sold at least as early as Jan. 1, 2000 to improve the decomposition of stored swine manure Jan. 1, 2000.

Gyles, C., Workshop #4: Enteric Diseases of Nursery Pigs, pp. 29-41, AASV 32nd Annual Meeting (2001), Nashville, Tenn.

Kim et at. "Aerobic nitrification-denitrification by heterothrophic Bacillus strains". Bioresource Technology. 2005, 96 pp. 1897-1906.

Office Action mailed Dec. 22, 2010 for U.S. Appl. No. 12/573,390, filed Oct. 5, 2009.

Office Action mailed Dec. 27, 2010 for U.S. Appl. No. 12/425,546, filed Apr. 17, 2009.

Office Action mailed Dec. 10, 2010 for U.S. Appl. No. 12/404,149, filed Mar. 13, 2009.

Hofacre, C L et al, "Subcutaneous Clostridial infection in broilers," Case Report, Avian Diseases vol. 30(3):620-622, 1986.

Hong, H. A. et al, "The use of bacterial spore formers as probiotics," FEMS Microbiol. Rev. (2005) 29:813-835.

Hungate, R. E. et al, "Microbiological and physiological changes associated with acute indigestion in sheep," Cornell Vet. (1952) 42:423.

Janstova, B. et al, "Heat Resistance of Bacillus spp. Spores Isolated form Cow's Milk and Farm Environment," Acta Vet.. Brno (2001) 70:179-184.

Jenny, B. F. et al, "Performance and fecal flora of calves fed a Bacillus subtilis concentrate," J. Dairy Sci. (1991) 74:1968-1973.

Jost B. H. et al, "Atypical cpb2 genes, encoding beta2-toxin in Clostridium perfringens isolates of nonporcine origin," Infect. Immun. (2005) 73:652-656.

/K/ "A multiple-strain product containing Bacillus strain BS 27 and strains other than those listed in the pending claims has been sold, at least as early as Jan. 1, 2000."

Karunakaran, D et al, "Use of antibiotics and its impact on gut microflora in turkeys," Am Avian Path, Philadelphia, PA, Aug. 2004.

Karunakaran, D, "Microbioligical challenges of commercial turkey flocks and methods of control," Poster #PP51 presented at AAAP Symposium on Poultry Vaccines and Vaccination Practices, Jul. 15-17, 2002.

Kennedy, C et al, "The A-toxin of Clostridium septicum is essential for virulence," Molecular Microbiology, 57(5): 1357-1366, 2005.

King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.

Kyriakis, S. C. et al, "The effect of probiotic LSP 122 on the control of post-weaning diarrhea syndrome of piglets," Res. Vet. Sci. (1999) 67:223-228.

La Ragione R M et al, "Bacillus subtilis spores competitively exclude Escherichia coli 078:K80 in poultry," Vet Microbiol 79:133-142, 2001.

La Ragione, R. M. et al, "Competitive exclusion by Bacillus subtilis spores of Salmonella enterica serotype Enteritidis and Clostridium perfringens in young chickens," Vet. Microbiol, (2003) 94:245-256.

Lu, J et al, "Diversity and succession of the intestinal bacterial community of the maturing broiler chicken," Applied and Environmental Microbiology, 69(11):6816-6824, Nov. 2003.

Marquardt, R et al, "Passive protective effect of egg-yolk antibodies against enterotoxigenic Escherichia coli K88+ infection in neonatal and early-weaned piglets," FEMS Immunology and Med Microbiology 23:283-288, 1999.

Marsh, T. et al, "Terminal restriction fragment length polymorphism analysis web-based research tool for microbial community analysis," Appl Environ Microbiol (2000) 66:3616-3620.

Maxwell, Jr., C. V. et al, "Feeding Weanling Pigs. In: Austin J. Lewis and Lee L. Southern (Ed.)," Swine Nutrition 2nd Edition. (2001) p. 691-717.

McCracken, B. A. et al, "Diet-dependent and diet-independent metabolic responses underlie growth stasis of pigs at weaning," J. Nutr. (1995) 125, 2838-2845.

McDonough, S. P., "Enteric pathogens in intensively reared veal calves," Am. J. Vet. Res. (1994) 55(11):1516-1520.

McMillan, K., "Foal pneumonia: An Illinois survey," An Health and Nutrit 34 (1986).

Morrill, J. L. et al, "Plasma proteins and a probiotic as ingredients in milk replacer," J. Dairy Sci. (1995) 78:902-907.

Mouricout, M. A. et al, "Inhibition of mannose-resistant haemagglutination of sheep erythrocytes by enterotoxigenic Escherichia coli in the presence of plasma glycoprotein glycans," FEMS Microbiol. Lett. (1986) 37:145-149.

Muir, L.A. et al, "Prevention of induced lactic acidosis in cattle by thiopeptin," J. Anim. Sci. (1981) 52:635.

Muyzer, G et al, "Profiling of complex microbial populations by denaturing gradient gel electrophoresis analysis of polymerase chain reaction-amplified genes coding for 16S rRNA," Applied and Environmental Microbiology, 59 (3):695-700, Mar. 1993.

Nagy, G et al, "Genetic diversity among Escherichia coli isolates carrying f18 genes from pigs with porcine postweaning diarrhea and edema disease," J Clinical Microbiology 37:5:1642-1645, May 1999.

Nagy, G et al, "Genetic diversity among Escherichia coli isolates carrying f18 genes from pigs with porcine postweaning diarrhea and edema disease," J Clinical Microbiology 37:5:1642-1645, May 1999.

NCBI gene bank accession #M59107.

NCBI gene bank accession #X73447.

Niilo, L., "Clostridium perfringens in animal disease: a review of current knowledge," Can. Vet. J. (1980) 21:141-148.
Nollet, H. et al, "Protection of just weaned pigs against infection with F18+ *Escherichia coli* by non-immune plasma powder," Vet. Microbiol. (1999) 65:37-45.
"Nonruminant Nutrition: weanling Pigs-additives" Online! 2004, pp. 25-28 XP002342561, Retrieved from the Internet: URL:http//www.fass.org/2004/abstracts/25.PDF> p. 26, col. 2, paragraph 3-5 [source: PCTUS2005/017141 ISR].
Owens, F. N. et al, "Acidosis in cattle: a review," J. Anim. Sci. (1998) 76:275-286.
Parrott, D et al, "Molecular typing of hemolytic *Escherichia coli* isolated from swine," Paper 385 (1 pg), Intl Pig Vet Soc, 2002.
Patterson, J A et al, "Application of prebiotics and probiotics in poultry production," Poultry Science 82:626-631, 2003.
Perez-Bosque, A. et al, "Dietary plasma protein affects the immune response of weaned rats challenged with *S. aureus*," Superantigen B. J. Nutr. (2004) 134:2667-2672.
Power, E. G., "RAPD typing in microbiology—a technical review," J. Hosp. Infect. (1996) 34(4):247-265.
Pyne, E et al, Prevalence and genetic diversity of *Clostridum perfringens* isolated from commercial turkey houses, Abstract #432 in Abstracts of papers.
Rehberger, T, "Genome analysis of *Propionibacterium freudenreichii* by pulsed-field gel electrophoresis," Current Microbiology 27(1):Jul. 21-25, 1993 (abstract).
Roche, K. C. et al, "Transforming growth factor beta-1 ameliorates intestinal epithelial barrier disruption by *Cryptosporidium parvum* in the absence of mucosal T lymphocytes," Infect. Immun. (2000) 68:5635-5644.
Roe, S, "Protein purification techniques," 2d Ed. Oxford U. Press, 172-175 (2001).
Sambrook, 3d Ed, 2001 (reference book, no specific cited or copy provided).
Slyter, L.L., "Influence of acidosis on rumen function," J. Anim. Sci. (1976) 43:910.
Snoeyenbos, G H, "Protecting chicks and poults from *Salmonellae* by oral administration of "normal" gut microflora," Avian Diseases 22(2):273-287, 1977.
Songer, J. G., "Clostridial enteric diseases of domestic animals," Clinical Microbiology Reviews (1996) 9(2):216-234.
Stable Fresh TM 1:3 concentrate, "An all natural USDA approved concentrate that eliminates stall odors for just pennies per day, per stall," Sterling Creek Enterprises (2 pgs).
"Table of Contents" Online! 2004, p. 1-4, XP002342560, retrieved from the Internet: URL:http://www.fass.org/2004/abstracts/>, p. 1, lines 1-14 [source: PCT/US05/017141 ISR].
Tam, N. K. M. et al, "The intestinal life cycle of *Bacillus subtilis* and close relatives," J. Bacteriol. (2006) 188:2692-2700.
Tang, M. et al, "Effect of segregated early weaning on postweaning small intestinal development in pigs," J. Anim. Sci. (1999) 77:3191.
Tanner, M. K. et al. "Respiratory and environmental effects of recycled phone book paper versus sawdust as bedding for horses," J Eq Vet Sci (1998) 468-476.
Tannock, G. W., "A special fondness for lactobacilli," Appl. Environ, Microbiol. (2004) 70:3189-3194.
Abe, F. et al, "Effect of administration of Bifidobacteria and lactic acid bacteria to newborn calves and piglets," J. Dairy Sci. (1995) 78:2838-2846.
Adami, A. et al, "Piglets fed from birth with the probiotic *Bacillus coagulans* as additive: zootechnical and microbiological aspects," Ann Microbiol Enzimol (1997) 47: 139-149.
Allison, M .J. et al, "Grain overload in cattle and sheep: Changes in microbial populations in the cecum and rumen," Amer. J. Vet Res. (1975) 36:181.
Awad, M M et al, "Synergistic effects of alpha-toxin and perfringolysin O in Clostridium perfringens-medicated gas gangrene," Infection & Immunity, 69(12):7904-7910, 2001.
Baker, A. et al, "Development of a *Bacillus subtilis* product for a large commercial swine farm to reduce Clostridium perfringens and Clostridium difficile in neonatal pigs," J. Anim. Sci. (2007) 85(suppl. 1):102.

Baker, G. C. et al, "Review and re-analysis of domain-specific 16S primers," Journal of Microbiological Methods (2003) 55:541-555.
Banach, S et al, "Prevalence, distribution and diversity of pathogenic *E. coli* in commercial turkey poult production," Presented at the Poultry Science Association Annual Meeting, Madison, WI, Jul. 2003.
Banach, S et al, "Prevalence, distribution and diversity of pathogenic *E. coli* in commercial turkey poult production," Poster #337, presented at the Poultry Science Association Annual Meeting, Madison, WI, Jul. 2003.
Barbosa, et al, "Applied and Environmental Microbiology," (Feb. 2005) vol. 71, 2:968-978.
Bembridge et al. "CD45RO expression on bovine T cells: relation to biological function," Immunology, (1995) 86:537-544.
Bertschinger, H U, "*Escherichia coli* infections," Diseases of Swine 8th Ed., Chap. 32, pp. 431-454, 1999.
Bikker, P. et al, "The influence of diet composition and an antimicrobial growth promoter on the growth response of weaned piglets to spray dried animal plasma." Livestock Prod. Sci. (2004) 86:201-208.
Billington et al., "Clostridium perfringens Type E animal enteritis isolates with highly conserved, silent enterotoxin gene sequences," Infect. Immun. (1998) 66(9):4531-4536.
Blood, D C, "Diseases caused by bacteria," Veterinary Medicine, 7th Ed., Bailliere, pp. 637-640, 1989.
Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.
Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.
Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.
Brosius, J et al, "Complete nucleotide sequence of a 16S ribosomal RNA gene from *Escherichia coli*," Proc Natl Acad Sci USA 75(10:4801-4805, Oct. 1978.
Brown, D. C. et al, "The influence of different management systems and age on intestinal morphology, immune cell numbers and mucin production from goblet cells in post-weaning pigs," Vet. Immunol. Immunopath (2006a) 111:187-198.
Brown, D. C. et al, "Ontogeny of T lymphocytes and intestinal morphological characteristics in neonatal pigs at different ages in the postnatal period," J. Anim. Sci. (2006b) 84:567-578.
Carr, D et al, "Excessive mortality in market-age turkeys associated with cellulitis," Avian Disease 40:736-741, 1996.
Cera, K. R. et al, "Effect of age, weaning and post-weaning diet on small intestinal growth and small intestinal morphology in young swine," J. Anim. Sci. (1988) 66:574.
Clean Air "HM Composter and Odor Eliminator," (1 pg).
Coffey, R. et al, "The impact of environment and antimicrobial agents on the growth response of early weaned pigs to spray-dried porcine plasma," J. Anim. Sci. (1995) 73:2532-2539.
Cooper, V, "Diagnosis of neonatal pig diarrhea, "Vet Clinics N Am Food Animal Practice, 16(1):117-161 (2000).
"Immediate release" 'Online! Jan. 13, 2005, pp. 1-2 XP002342562, retrieved from the Internet: URL: http://www.agtechproducts.com/press/DSM_Market_Microsource.pdf>, p. 1, line 1-line 15, p. 2, paragraph 4-last paragraph. [source: PCT/US05/017141 ISR].
Cromwell, G. L., "Antimicrobial and promicrobial agents. In: A. J. Lewis and L. L. Southern (eds.)," Swine Nutrition. p. 611. CRC Press, Boca Raton, FL (2001).
Cruywagen, C. W. et al, "Effect of *Lactobacillus acidophilus* supplementation of milk replacer on preweaning performance of calves," J. Dairy Sci. (1996) 79:483-486.
Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M.E. et al, "Comparison of direct-fed microbial and antibiotic supplementation on innate and adaptive immune characteristics of weaning pigs," Reprod. Nutr. Dev. (2006) 46(Suppl.1):S63.

Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.

Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Dean-Nystrom, E et al, "Edema disease: a re-emerging problem?," Am Assoc of Swine Veterinarians, pp. 223-224, 2001.

Donald, J, "Treating poultry house floors to improve performance," The Poultry Engineering, Economics & Management Newsletter, Issue No. 23, 4 pgs, May 2003.

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Francis, D, "Post-weaning *E. coli*-diagnosis, treatment, control, and its effect on subsequent growth performance," Am Assoc of Swine Veterinarians, 495-499, 2004.

Fritts, C A et al, "*Bacillus subtilis* C-3102 (Calsporin) improves live performance and microbioligical status of broiler chickens," Applied Poultry Science, Inc., 9:149-155, 2000.

Fuller, R., "Introduction. In: R. Fuller (Ed.). Probiotics 2: applications and practical aspects," Chapman and Hall, New York. (1997) p. 1.

Gaskins, H. R., "Intestinal bacteria and their influence on swine growth in: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a Bacillus-based direct-fed microbial on turkey poult performance and changes within the gastrointestinal microflora," J. Anim. Sci. (2007) 85(suppl. 1):249.

Grimes, J L et al, "Heat treatment of turkey litter for reuse as bedding," Int J of Poultry Science 2(5):287-292, 2003.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

* cited by examiner

BACILLUS STRAINS USEFUL AGAINST CALF PATHOGENS AND SCOURS

CROSS REFERENCE TO RELATED PATENT APPLICATION

This application claims priority under 35 U.S.C. §119(e) to U.S. Provisional Patent Application No. 61/078,708, filed Jul. 7, 2008, the entirety of which is incorporated by reference herein.

BIBLIOGRAPHY

Complete bibliographic citations of the references referred to herein by the first author's last name in parentheses can be found in the Bibliography section, immediately preceding the claims.

FIELD DESCRIBED HEREIN

The invention relates to controlling calf pathogens and scours. More particularly, the invention relates to using *Bacillus* strains for controlling calf pathogens and scours and methods.

DESCRIPTION OF THE RELATED ART

Dehydration in calves is commonly treated with electrolyte replacement therapy which is an effective treatment; however, electrolyte supplements do not treat the primary cause of dehydration: bacterial, coccidial, and viral associated scours (diarrhea). Scours are important economically due to high prevalence of affected calves (McDonough, 1994), dehydration associated weight loss (Cruywagen et al. 1996), mortalities (Abe et al., 1995), and medication costs (Morrill et al., 1995; Timmerman et al., 2005). Management plays an important role in mitigating the effects of scours. However, alterations in management to prevent scours are difficult as scours are a result of interactions between infectious agents, stress levels, nutrition, lack of or insufficient passive immunity transferred via colostrum, and immune development (McDonough, 1994). Due to the complexity of these interactions, it is difficult to anticipate scour prevalence; therefore, novel agents for the prevention and treatment of scours are of interest.

A bacterium frequently implicated as a causative agent of scours is *Clostridium perfringens* (Vance, 1967; Niilo, 1980; Songer, 1996). However, there is a paucity of data surveying calf and farm level *C. perfringens* prevalence. *C. perfringens* is a ubiquitous, gram-positive, spore-forming bacterium that can reside in the environment and in mammalian and avian gastrointestinal tracts (GIT) (Hatheway, 1990; Songer, 1996; Jost et al., 2005). It is unknown whether differences in pathogenicity are due to *C. perfringens* strain, abundance of *C. perfringens*, or host health status.

Direct-fed microbial (DFM) products have been used as competitive inhibition agents and the use of DFM products are becoming a popular alternative to antibiotic use in livestock species. DFM products provide benefits by several mechanisms, e.g., restricting adherence of pathogenic microbes to mucosal surfaces, stimulating immune responses, stimulating proliferation of other beneficial microorganisms, and producing antimicrobial substances (Abe et al., 1995; Tam et al., 2006; Wu et al., 2006). *Bacillus*-based DFM products fulfill a number of these mechanisms (Jenny et al., 1991; La Ragione et al., 2001; Hong et al., 2005), and *Bacillus*-based products have been available for human use for decades. Some studies have observed beneficial results of feeding DFM products to neonatal calves including increased body weight gain, increased ADG, improved feed efficiency and feed conversion, and improved fecal scores (Abe et al., 1995; Timmerman et al., 2005). Studies have shown similar results between feeding DFM products and prophylactic levels of antibiotics for growth and performance (Morrill et al., 1995; Donovan, 2002) indicating that DFM products may be useful as a compliment or alternative to antibiotics.

DFM products have shown efficacy as competitive exclusion agents (La Ragione et al., 2001) and as growth promoters (Abe et al., 1995).

DFM products have reduced *C. perfringens* shedding in vivo (La Ragione and Woodward, 2003; Gebert et al., 2007) and *C. perfringens* growth in vitro (Gebert et al., 2006; Baker et al., 2007). However, a shortcoming of this is that decreases in shedding alone are not indicative of increases in calf health and productivity.

Some DFM products have been efficacious in modulating neonatal calf scours (Timmerman et al., 2005). However, these DFM products may have had limited shelf life viability due to the usage of non-spore forming strains, thus, limiting the routes of administration or modes of delivery to the calf.

In view of the foregoing, it would be desirable to provide one or more *Bacillus* strains for controlling calf pathogens and scours and for improving calf growth.

SUMMARY OF THE INVENTION

The invention, which is defined by the claims set out at the end of this disclosure, is intended to solve at least some of the problems noted above.

A composition is provided that includes *Bacillus subtilis* strains 3A-P4 ATCC Accession No. PTA-6506, 22C-P1 ATCC Accession No. PTA-6508, and LSSA01 NRRL Accession No. NRRL B-50104.

A method is also provided in which an effective amount of a composition comprising *Bacillus subtilis* strains 3A-P4 ATCC Accession No. PTA-6506, 22C-P1 ATCC Accession No. PTA-6508, and LSSA01 NRRL Accession No. NRRL B-50104 is administered to a calf.

In at least some embodiments of the invention, the method provides at least one of the following benefits in a calf administered the composition, when compared to calves not administered the composition: controlling pathogens in the calf, controlling scours in the calf, improving weight gain of the calf, inhibiting at least one of *Clostridium, E. coli*, and *Salmonella* pathogens in the calf, reducing treatments in the calf, reducing total treatment expenditures for the calf, reducing fecal shedding of presumptive *Clostridium* in the calf, enhancing immune development in the calf, increasing weight gain in the calf, reducing inflammatory response in the calf, and maturing the immune system of the calf by stimulating the immune system.

In at least some embodiments of the invention, the method inhibits *C. perfringens* type A pathogens in the calf.

In some embodiments of the invention, the *Bacillus* strains in the composition administered to the calf are modified based on a change in pathogenic strains to which the calf is exposed.

BRIEF DESCRIPTION OF THE DRAWINGS

Preferred exemplary embodiments described herein are illustrated in the accompanying drawings, in which like reference numerals represent like parts throughout and in which.

DETAILED DESCRIPTION

Figure 1:
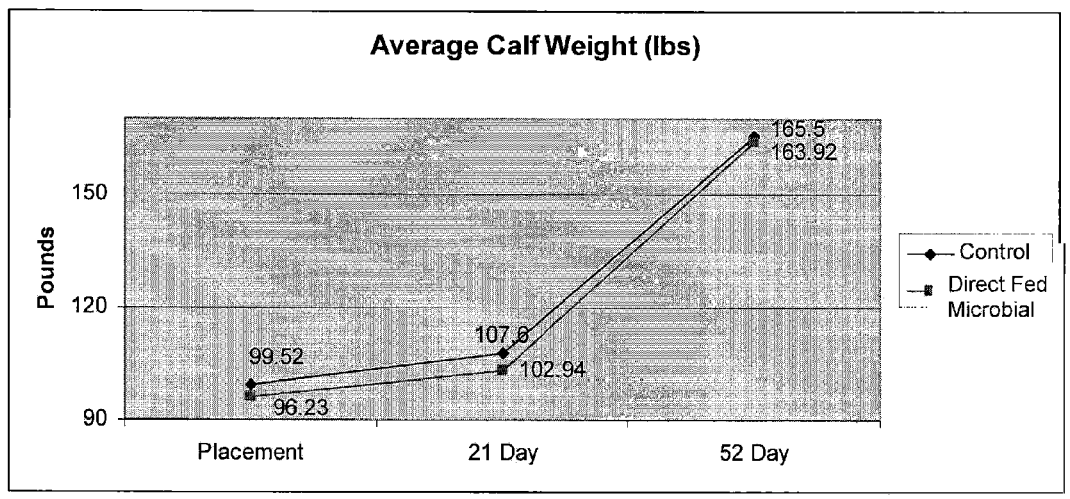
FIG. 1 is a graph showing average calf weight between treated and control calves showing that despite treated calves weighing less at the beginning of the study, calves in the treated group gained such that there was no difference between the treated and control group a the end of the study.
Figure 2:
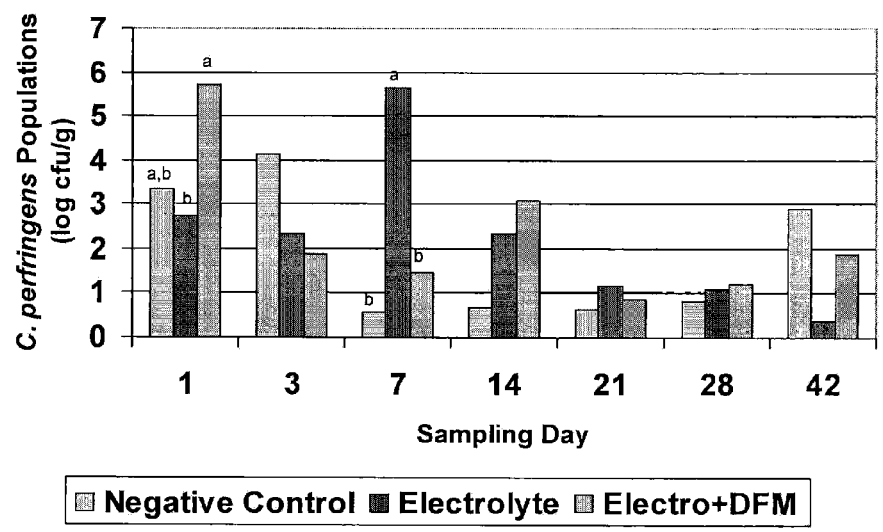
FIG. 2 is a graph showing presumptive *Clostridium perfringens* fecal shedding by dairy calves, which were never treated for scours (non-scouring), treated with electrolyte therapy for scours, or treated with the electrolyte therapy containing a *Bacillus*-based direct fed microbial, at each sampling day of the 8-week trial (trt x day interaction, P=0.02). $^{a,b}$Means without common superscripts are significantly different (P≦0.05) within days Before explaining embodiments described herein in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

Provided herein are compositions that include three *Bacillus* strains useful for controlling calf pathogens and scours. Methods of making and using the *Bacillus* strains are also provided. The compositions are highly stable, and thus, they have a long shelf life.

*Bacillus* Strains:

*Bacillus* strains have many qualities that make them useful for controlling calf pathogens and scours and methods of making and using the *Bacillus* strains. For example, Bacillus strains produce extracellular enzymes, such as proteases, amylases, and cellulase. In addition, Bacillus strains produce antimicrobial factors, such as gramicidin, subtilin, bacitracin, and polymyxin. Several *Bacillus* species also have GRAS status, i.e., they are generally recognized as safe by the US Food and Drug Administration and are also approved for use in animal feed by the Association of American Feed Control Officials (AAFCO). All *B. subtilis* strains are GRAS.

The *Bacillus* strains described herein are aerobic and facultative sporeformers and thus, are stable. *Bacillus* species are the only sporeformers that are considered GRAS.

*Bacillus* strains found to be useful in the compositions provided herein include *B. subtilis* strains 3A-P4, 22C-P1, and LSSA01. On Jan. 12, 2005, strains 3A-P4 and 22C-P1 were deposited at the American Type Culture Collection (ATCC), 10801 University Blvd., Manassas, Va. 20110-2209 and given accession numbers PTA-6506 (3A-P4) and PTA-6508 (22C-P1), respectively. Strain LSSA01 was deposited on Jan. 22, 2008 at the Agricultural Research Service Culture Collection (NRRL), 1815 North University Street, Peoria, Ill., 61604 and given accession number NRRL B-50104. All of the deposits were made under the provisions of the Budapest Treaty on the International Recognition of the Deposit of Microorganisms for the Purposes of Patent Procedure.

*Bacillus* strains 3A-P4 and 22C-P1 were isolated from different geographical regions of North America and from different environmental sources. Specifically, strain 3A-P4 was isolated from chicken litter from Canada, and strain 22C-P1 was isolated from a swine lagoon from the Eastern United States.

*Bacillus* strains 3A-P4, 22C-P1, and LSSA01 are combined to form a composition. Combinations of other *Bacillus* strains can be used based on the pathogenic strains present in a specific production facility or other environment. That is, the combination of *Bacillus* strains can be modified if the pathogenic strains change.

Although not intended to be a limitation to the present disclosure, it is believed that inhibition of pathogens is accomplished via the secretion of an active metabolite from the *Bacillus*.

Preparation of the *Bacillus* Strains:

The *Bacillus* strains are grown in a liquid nutrient broth, preferably to a level at which the highest number of spores are formed. In one embodiment, the strains are grown to an OD where the spore yield is at least $1 \times 10^9$ colony forming units (CFU) per ml of culture. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

The *Bacillus* strains of the present invention are produced by fermentation of the bacterial strains. Fermentation is started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

The count of the culture can then be determined. At the time of manufacture, the *Bacillus* count preferably is at least about $1.0 \times 10^{11}$ CFU/g. The counts may be increased or decreased from this number and still have complete efficacy.

To prepare the compositions, the cultures and carriers (where used) can be added to a ribbon or paddle mixer and mixed preferably for about 15 minutes, although the timing can be increased or decreased. The components are blended such that a uniform mixture of the cultures and carriers result. The final product is preferably a dry, flowable powder.

Making and Using the Compositions:

The compositions provided herein include *B. subtilis* strains 3A-P4, 22C-P1, and LSSA01. In at least one embodiment, equal amounts (based on colony forming units (cfu)) of each strain are used. For example, where three strains are used, one-third of each strain is used to arrive at the total dosage. However, differing amounts can also be used. In at least some embodiments, the compositions include one or more carriers.

The *Bacillus* strains can be used in direct-fed microbials, that is, they can be fed directly to animals, such as cattle. In one embodiment, the composition is fed to a calf from birth to 56 days in age. The direct-fed microbial can also be fed in other forms and to cattle of different ages, e.g., to adult cattle and to calves of other ages.

*Bacillus* strains described herein may also be presented in various forms, for example as a top dress, liquid drench, gelatin capsule, or gel. *Bacillus* strains may also be added to a milk replacer. Milk replacers are typically milk substitutes in powdered form that are mixed with water to form a composition that resembles milk.

In at least one embodiment, the *Bacillus* strains may be added to milk replacer when calf milk replacer is packaged or as an addition to calf milk replacer prior to feeding. In one embodiment of adding the *Bacillus* strains in a milk replacer, the strains are included at a rate of $2 \times 10^9$ CFU/head/day to provide a prophylactic affect at controlling bacterial associated neonatal calf scours.

In addition, Bacillus strains may be added to commercially available electrolytes. In at least one embodiment, the *Bacillus* strains are administered to calves experiencing scours as a therapeutic dose consisting of $3 \times 10^9$ CFU/dose. Calves may be administered multiple doses until the calf is no longer scouring or until dehydration no longer persists.

In one embodiment of the top dress form of the strains, freeze-dried *Bacillus* fermentation product is added to a carrier, such as whey, maltodextrin, sucrose, dextrose, limestone (calcium carbonate), rice hulls, yeast culture, dried starch, sodium silico aluminate. In one embodiment of the liquid drench, freeze-dried *Bacillus* fermentation product is added to a carrier, such as whey, maltodextrin, sucrose, dextrose, dried starch, sodium silico aluminate, and a liquid is added to form the drench. In one embodiment of the gelatin capsule form, freeze-dried *Bacillus* fermentation product is added to a carrier, such as whey, maltodextrin, sugar, limestone (calcium carbonate), rice hulls, yeast culture dried starch, and/or sodium silico aluminate. The *Bacillus* strains and carrier are enclosed in a degradable gelatin capsule. In one embodiment of the gel form, freeze-dried *Bacillus* fermentation product is added to a carrier, such as vegetable oil, sucrose, silicon dioxide, polysorbate 80, propylene glycol, butylated hydroxyanisole, citric acid, and artificial coloring to form the gel. In all of the examples, one or more carriers can be used.

Administration of the direct-fed microbial to calves is accomplished by any convenient method, including adding the *Bacillus* strains to the animals' drinking water, to their feed, or by direct oral insertion, such as by an aerosol. In at least some embodiments, calves are fed the direct-fed microbial in a milk replacer. In at least some embodiments, calves are fed the direct-fed microbial in electrolytes. *Bacillus* strains preferably are administered as spores.

The following dosages are for all of the *Bacillus* strains that are fed. That is, the CFU is of all of the *Bacillus* strains. In at least some embodiments, the composition is administered at a rate of about $2 \times 10^9$ CFU/calf/day. This dosage is useful as a prophylactic dosage. In at least some other embodiments, the composition is administered at a rate of about $3 \times 10^9$ CFU/calf/day. This dosage is useful as a therapeutic dosage. However, other dosages can be used, and the listed dosages can be used for other purposes.

In at least one embodiment of the liquid drench and gel, each has about $1 \times 10^4$ CFU/g or ml/day to about $1 \times 10^{11}$ CFU/head/day. In another embodiment of the liquid drench and gel, each has about $3 \times 10^9$ CFU/head/day. In at least one embodiment of the top dress, basemix, and premix, each includes about $1 \times 10^3$ CFU/g of feed to about $1 \times 10^{10}$ CFU/g of feed. In other exemplary embodiments of the top dress, basemix, and premix, each uses about $5.0 \times 10^{10}$ CFU/g of product, i.e., top-dress, basemix, or premix, that is added to feed at 3.2 kg/ton of feed to provide $1.76 \times 10^8$ CFU/g of feed. In one embodiment of a dosage for inclusion into water, about $1 \times 10^3$ CFU/animal/day to about $1 \times 10^{11}$ CFU/animal/day is used. In some embodiments about $1 \times 10^8$ CFU/animal/day is included in water. While these examples use freeze-dried *Bacillus* as an ingredient in the top dress, liquid drench, gels, water, and feed forms, it is not necessary to freeze-dry the *Bacillus* before feeding it to animals. For example, spray-dried, fluidized bed dried, or solid state fermentation *Bacillus* or *Bacillus* in other states may be used. The strains can also be administered in a wet cell slurry paste, with or without preservatives, in concentrated, unconcentrated, or diluted form.

EXAMPLES

The following Examples are provided for illustrative purposes only. The Examples are included herein solely to aid in a more complete understanding of the presently described invention. The Examples do not limit the scope described herein described or claimed herein in any fashion.

Example 1

Introduction.

*Clostridium perfringens* Type A, pathogenic *E. coli*, and *Salmonella* spp. have been associated with scours in calves; however, there is a lack of data characterizing the bacterial genotypes of these pathogens in calves. Therapies and prophylaxes are available for these bacterial pathogens; however, these products typically were either not designed specifically for reducing these pathogens or were designed against only a few isolates.

Materials and Methods.

A survey of *C. perfringens*, pathogenic *E. coli*, and *Salmonella* spp. in calves was performed with the objectives of assessing prevalence and genotypes of these pathogens. Genotyping results were utilized to develop a *Bacillus*-based direct fed microbial (DFM) that inhibited a broad range of *C. perfringens* virulent *E. coli*, and *Salmonella* spp. 705 fecal swabs and 108 gastrointestinal tract samples were collected from scouring calves in California, Iowa, Ohio, Pennsylvania, Washington, and Wisconsin. Randomly Amplified Polymorphic DNA Polymerase Chain Reaction and BioNumerics software (Applied Maths Inc. Austin, Tex.) were utilized to create genetic fingerprints and to assess genotypic diversity of these pathogens. For *C. perfringens*, virulent *E. coli*, and *Salmonella* spp., 917, 126, and 181 colonies were isolated, respectively.

Results.

All isolates were *C. perfringens* Type A. The results of the *C. perfringens* genotypic survey indicate that there were 149 genotypes at 75% similarity using the Dice similarity coefficient with the unweighted pair group method using arithmetic averages. Similar analysis revealed 17 and 64 unique genotypes at 80% similarity for virulent *E. coli* and *Salmonella* spp., respectively. Representatives of all unique genotypes were utilized in an inhibition assay to determine percent inhibition of these pathogens by the filtrates of six *Bacillus* strains. Of the six, three *Bacillus* strains were selected from this analysis: strains 3AP4, 22C-P1, and LSSAO1. Together the three *Bacillus* strains inhibited 89% of the *C. perfringens*, 100% of the *E. coli*, and 99% of the *Salmonella* spp.

Example 2

Summary:

A direct-fed microbial including *Bacillus* strains 3AP4, 22C-P1, and LSSAO1 was administered in milk replacer to calves in a first group receiving the direct-fed microbial and compared to calves in a second group not fed the direct-fed microbial (the control group). Calves fed the direct-fed microbial tended ($p<0.118$) to improve 52 day weight gain ending the trial with nearly +3 lbs added gain versus the control group. During the second week of the study, which was the peak disease challenge period, the group receiving the direct-fed microbial had reduced treatments 56% over the control group. Total treatment expenditures were reduced $0.67/calf in the group receiving the direct-fed microbial versus the control group. Mortality was not affected by the direct-fed microbial. In fact, seven calves died in the group receiving the direct-fed microbial versus five in the control group. The direct-fed microbial did not reduce incidence of *Clostridium perfringens* type A as noted in 112 fecal swabs, despite 25% of randomly pulled swabs indicating presence of the disease. Swabs did not detect *Clostridium perfringens* type B, C or D or *Salmonella*. Only two calves noted incidence of virulent strains of *E. coli*. Impact might have been greater with significant incidence of *Salmonella* or *E. coli*. Also, it is worth noting the calves in the group receiving the direct-fed microbial started significantly less in weight at placement (p<0.06) and trended lower at 21 days (p<0.175). Its remarkable weight gain advantage was +3 lbs for calves in the group receiving the direct-fed microbial versus the calves in the control group at 52 days, indicating that perhaps this difference would become even more pronounced at later stages of production.

Materials and Methods:

The trial was conducted in a 120 stall mechanically ventilated veal production facility in Wisconsin. One hundred twenty sale barn sourced Holstein bull calves were randomly and equally placed in treatment and control groups on May 1st (35 head), 2nd (28 head), 3rd (27 head) and 4th (30). Individual scale weights were measured the morning of May 5th and all calves in even-numbered stalls received 1 gram ($1 \times 10^9$ CFU) of the *Bacillus* strains 3AP4, 22C-P1, and LSSAO1, with equal counts of each of the three strains, the CFU being a total microbial count of all of the *Bacillus* strains, in the morning (May 5) milk feeding and each feeding thereafter for a total dose of $2 \times 10^9$ CFU/animal/day. The every-other-calf study design eliminates variability in calf placement, ventilation or grower feeding practices. All calves started directly on milk replacer at placement (w/o the direct-fed microbial). The calves were started on 6.4 oz (3 lbs solution) per calf per feeding of a 20:20, all milk formula (Anderson Calf Milk 20:20 non-medicated milk replacer with BioMos 3.4 grams/day at 10 oz feeding rate). Feeding rate increased approximately 0.5 oz daily over a 10 day period (see Table 1 below) to a maximum of 10 oz milk replacer per feeding (5 lbs solution). The 10 oz feeding rate was continued through 53 days when feeding rate was reduced to once a day. Calves were fully weaned at 55 days. Milk replacer was mixed with hot water and fed at approximately 5:30 AM and 5:00 PM each day. The grower was provided with individual, foil, heat-sealed pouches that contained 60 grams of the direct-fed microbial, which was a water-soluble formulation containing 1 billion CFU/g of carrier, which consisted of bakers sugar, dextrose and baylith.

TABLE 1

20:20 All-Milk formula Feeding Regiment, 2 feedings per day

| Day | Oz of Solids/Calf/Feeding |
|---|---|
| Placement | 6.4 |
| Day 1 of trial | 6.4 |
| 2 | 7.1 |
| 3 | 7.8 |
| 4 | 8.3 |
| 5 | 8.3 |
| 6 | 7.5 |
| 7 | 8.0 |
| 8 | 8.5 |
| 9 | 9.0 |

TABLE 1-continued

20:20 All-Milk formula Feeding Regiment, 2 feedings per day

| Day | Oz of Solids/Calf/Feeding |
|---|---|
| 10 | 9.5 |
| 11-42 | 10 |
| 43-55 | 5 |

Milk replacer was blended and calves in the control group were fed. The direct-fed microbial was then blended in the tank and all treatment calves were fed. Spray dried plasma was incorporated into a 20:20 milk formula at 4.4% starting on day 24 in the study through weaning. With the exception of addition of the direct-fed microbial, milk solutions were identical for the group receiving the direct-fed microbial and the control group throughout the trial. A texturized 18% CP, 7% fat calf starter feed with 33 g/ton Rumensin (Vita Plus Calf Power Starter) was introduced on day 15 of the trial at 8 oz/calf/feeding. Every calf got the same amount of starter feed throughout the trial. Tank mix antibiotics were incorporated in milk replacer solution and fed to all calves according to Table 2 below.

TABLE 2

Tank Mix Antibiotics
Tank-Mix Antibiotic Regiment

| Day 1-10 | Deccox L 1.5 lbs p/feeding |
|---|---|
| Day 5-12 | Neo 325 (200 g) 1 pack p/feeding |
| Day 5-12 | OTC (100 g) 1 cup (8 oz) p/feeding |
| Day 5-8 | SMZ 2 pills per calf p/feeding |
| Day 20-25 | Auromycin Sulmet 3 packs p/feeding |

Calves were individually ear tagged with corresponding stall number upon placement. Twenty pairs (40 calves) were selected for collection of fecal swabs. Swabs were collected on all 40 calves at day 6, 8 (peak scours) and 15 in the trial. Pairs of calves were selected to be evenly dispersed throughout the room. In each pair one was a treatment and one was a control calf Swabs were sent overnight to Agtech Products, Inc. for presumptive screening and further exact genetic identification using multi-plex PCR analysis for *Clostridium perfringens* type A, B, C & D, presence of *Salmonella*, and virulent strains of *E. coli*. Blood samples from the same 40 calves were drawn at day 6 of the trial using serum separator tubes. Samples were analyzed for total protein by a recognized industry expert regarding calf immunology. The grower measured calf weights on the entire 120 calves directly after the room was full (May 5) and again at day 21 (May 25) and day 52 (June 25). The grower recorded all treatments, feed refusals and death losses.

Results and Discussion:

Despite random placement, calves in the group receiving the direct-fed microbial were 3.3 pounds lighter at placement (p<0.06) than the control group. This weight difference became greater at 21 days (4.66 lbs) and total gain from day 1-21 tended lower (p<0.175) for the calves receiving the direct-fed microbial when compared to the calves in the control group. It is remarkable that total gain in calves receiving the direct-fed microbial was 2.92 lbs heavier at 52 days than in the control group (p<0.118). A significant disease challenge occurred the second week in the barn, and 28% of calves in the room were treated with therapeutic antibiotic regimens consisting of Nuflor (Schering-Plough Animal Health Corp., Summit, N.J.), Excenel (Pfizer, Inc., New York, N.Y.), cephalexin, penicillin, Baytril (Bayer Healthcare LLC, Shawnee Mission, Kans.), or SMZ. Anti-inflammatory treatments may have been administered concurrently with antibiotic regimens and consisted of dexamethazone, and/or Banamine (Schering-Plough Animal Health Corp., Summit, N.J.). Corid (Merial LTD., Duluth, Ga.) may have been administered if calf was suspected to be suffering form coccidia related scours. Immune stimulating therapies such as Immunoboost (Bioniche Animal Health USA, Inc., Bogart, Ga.) may have also been administered. Calves receiving the direct-fed microbial noted a 56% reduction in number of treatments during this enteric and respiratory disease challenge than calves in the control group (week 2, see Table 3 below).

TABLE 3

Total Number of Treatments

| | CONTROL | PROBIOTIC |
|---|---|---|
| Week 1 | 0 | 0 |
| Week 2 | 57 | 25 |
| Week 3 | 20 | 14 |
| Week 4-8 | 0 | 0 |

Total injectible treatment expenditures were reduced $40.55 or 54% in the calves receiving the direct-fed microbial versus the calves in the control group. Total injectible expenditures in the control group were $74.85 vs. $34.30 in the calves receiving the direct-fed microbial. Twenty-five (42%) of control calves received one or more treatments during the study versus 20 (33%) in the direct-fed microbial treated group. Mortality was not affected by the direct-fed microbial. Seven calves receiving the direct-fed microbial (11.7%) died versus five (8.3%) in control group. All mortality occurred during the week two and three disease challenge period. Seventy percent of calves in the room recorded failure of passive transfer (total protein less than 5.0). There was no difference in average total protein or percent FPT between the groups. Twenty four of 112 total fecal swabs gathered in the room were positive for *Clostridium perfringens* type A and there was no difference in incidence of the disease between treatment and control. Two swabs in the control group were positive for virulent strains of *E. coli*. No presence of *Clostridium perfringens* type B, C, D or *Salmonella* was detected in any swab. It should be noted that these swabs were from random selected pairs of calves that were not necessarily scouring. Fewer feed refusals were noted in the calves receiving the direct-fed microbial than in calves in the control group during the week two disease challenge. However, very few refusals were noted in the study.

Example 3

Summary:

Supplementation of a commercial electrolyte product with a *Bacillus*-based direct-fed microbial (DFM) at the onset of scours increased gain, reduced *C. perfringens* fecal shedding, reduced therapeutic medication expenditures, and enhanced immune development in dairy calves. Scours promoted the development of a more mature immune system; however, supplementation with the DFM seemed to further enhance development of the T cell repertoire later in the study. The DFM also alleviated the inflammation from scours earlier than with electrolyte alone; however, both electrolyte treatments decreased inflammatory cell populations later in the study, allowing more energy for growth at this time point. Finally, the DFM altered immune cell populations in scouring calves to resemble those of non-scouring calves. This immunomodulation coincided with a decrease in *C. perfringens* fecal shedding in scouring calves during week one to concentrations similar to those witnessed in the feces of non-scouring calves. These results indicate that the immunomodulatory effects of the DFM and the reduction in *C. perfringens* via the DFM resulted in the calves appearing immunologically similar to the non-scouring calves, suggesting supplementation with the DFM resolved the *C. perfringens* challenge in scouring calves more quickly that calves provided only electrolyte therapy. Providing this DFM as a supplement to electrolyte therapy was an acceptable therapeutic treatment for scours as evidenced by a reduction in *C. perfringens*, increased gain, reduced medication cost, and quiescence of inflammatory responses along with stimulation of immune system leading to maturation.

Materials and Methods:

Allocation of Animals:

A total of 65 Holstein bull calves were housed in individual hutches. All calves were purchased on the same day at one sale barn. Day of placement was considered day 0 of the trial. All calves were fed a non-medicated 20/20 milk replacer (20% CP and 20% fat) for the duration of the trial. Calves were offered a commercial starter feed ad libitum throughout the trial. The trial encompassed an eight week period. Fecal scores ranging from 1 to 3 were assigned daily with 1 being firm and 3 being loose. Calves were considered to be scouring with a fecal score of 3. Intake was monitored daily. Calves were weighed weekly. Mortalities and all treatments were recorded daily. Calves were weaned at 42 days post-placement.

Calves were divided into three treatment groups as described below:

Treatments:
1) A negative control in which the calves never scoured and therefore received no electrolyte treatment. (Negative Control)
2) A control electrolyte drench (Blue Ribbon, Merrick's, Inc., Union Center, Wis.) was used as a supportive therapy for scouring calves. (electrolyte)
3) The same electrolyte drench containing a *Bacillus*-based DFM ($3 \times 10^9$ cfu/dose, the DFM including *Bacillus* strains 3AP4, 22C-P1, and LSSAO1 with equal counts of each of the three strains). (electrolyte+DFM)

On each day, as scours were detected, the calves were assigned to treatment, such that the first calf (by calf ID#) was provided the control electrolyte treatment and the next was provided the electrolyte+DFM. As soon as incidence of scouring was noticed, a fecal score was assigned to the calf, and the calf received mandatory electrolyte treatment in the AM for two days. Scouring calves were evaluated to determine severity of scours and whether an additional therapeutic electrolyte dose was needed in addition to the mandatory AM dosings for two days. Additional rehydration therapy occurred in addition to the AM electrolyte dosing based on calf condition as determined by evaluation of skin elasticity, responsiveness, alertness, and strength of the calf. The evaluation is outlined below:
1) Slightly dehydrated—the calf's skin tents very little. Calf received an additional dose of electrolyte that day at ~2:00 PM.
2) Moderately dehydrated—the calf's skin tents 1-2 seconds. Calf received an additional dose of electrolyte that day in the PM and one ringer in the AM.

3) Very dehydrated—the calf's skin tents for more than 2 seconds. Calf received an additional dose of electrolyte that day in the PM and two ringers (AM and PM).

4) Severely dehydrated—the calf was near death. Calf received an additional dose of electrolyte that day, two ringers in the AM and PM, plus however many ringers were needed to keep the calf alive.

Sampling Dates:

Calves were placed on the pad on the afternoon. A routine receiving protocol was performed on all calves that afternoon, and all calves received a half-dose of electrolyte devoid of DFMs. The following morning, scouring calves were treated with electrolyte or electrolyte+DFM according to the protocol described above. After the calves were fed, evaluated, and treated, 24 calves without incidence of scours were selected for blood and fecal sampling on day 1 and formed the 24 calves that made up the negative control pool. On subsequent sampling days, calves were fed, evaluated and treated according to trial protocol described above, after which blood and fecal samples were obtained from treated and negative control calves. Calves that began treatment the morning of sampling were not considered a "treated" calf until the next sampling date. Calves that were treated any day prior to the morning of the sampling date were considered "treated."

Determination of Fecal Microbial Populations:

Selection of Calves for Fecal Sampling:

Fecal samples were obtained from 21 randomly selected calves without incidence of scours on the day following placement (d 1). Additional fecal samples were collected on d 3, 7, 14, 21, 28, and 42 post-placement. An attempt was made to sample eight calves in each treatment (scouring calves treated with electrolyte+DFM, scouring calves treated with electrolyte supplement, and calves with no incidence of scouring) from the initial pool of 21 calves on each sampling day after scours were detected. If eight scouring calves from each electrolyte treatment were not available from the 21 calves initially sampled, samples were obtained from other scouring calves.

Fecal Sample Collection and Microbial Analysis:

Only freshly deposited fecal samples or fecal grabs were analyzed. An approximately 10 g sample was obtained from the calves. Upon arrival at Agtech, the fecal samples were weighed and diluted in 0.1% sterile peptone. The diluted samples were stomached using a masticator (IUL, S.A., Barcelona, Spain) for 60 seconds at 6 strokes per second. Samples were spiral plated (Autoplate 4000, Spiral Biotech, Inc., Norwood, Mass.) for the enumeration of *Clostridium* on *C. perfringens* agar (Oxoid Limited, Hampshire, UK) supplemented with 400 µg mL$^{-1}$ tryptose sulfite cycloserine (TSC, Oxoid) and egg yolk emulsion 50 µL mL$^{-1}$ (Oxoid). Plates were incubated for two days, anaerobically with gas packs (Mitsubishi Gas Chemical Co., Inc., New York, N.Y.), at 37° C. and counted. Up to five putative *C. perfringens* colonies were picked from the agar plates into Reinforced Clostridial Broth (BD, Franklin Lakes, N.J.) and incubated anaerobically (Mitsubishi) for one day. After incubation, the broth-culture was split into two falcon tubes (Biologix, Lenexa, Kans.) and the bacterial cells were harvested by centrifugation (Eppendorf Centrifuge 5804, Hamburg, Germany) at 4500×g for five minutes. The supernatant was poured off, and the pellet was resuspended in either 1 mL $T^{50}E^{50}$ 15% sucrose (pH=8) for DNA extraction or 4 mL Reinforced Clostridial Broth (BD) containing 10% glycerol and frozen at −80° C. for future culturing.

Molecular Confirmation of Presumptive *C. perfringens:*

DNA was extracted using a commercially available kit (Roche, Basel, Switzerland) and a multiplex Polymerase Chain Reaction (mPCR) (Billington et al., 1998) was performed to identify if any of the isolates carried any of the four major *C. perfringens* toxin genes (α, β, ϵ, and τ) or other genes associated with virulence (enterotoxin and β2 toxin). The 50 μl mPCR reactions were performed in a thermal cycler (AB GeneAmp PCR System 2700, Epsom, UK); each reaction contained: 3 μL template DNA, 5 μL 10×PCR buffer (Invitrogen, Carlsbad, Calif.), 2 μL 50 mM $MgCl_2$, 1 μL 10 mM deoxynucleoside triphosphate mixture (Roche), 26.5 μl, twice sterilized water, 25 pmol of each primer, and 5 units of Taq polymerase (Invitrogen). Thermal cycler conditions were 5 min at 94° C. followed by 30 cycles of 55° C. for 1 min, 72° C. for 1 min, and 94° C. for 1 min mPCR products were separated via electrophoresis (PowerPac Basic, Bio-Rad) in 3% (w/v) NuSieve agarose gels (Bio-Rad, Hercules, Calif.) with 0.5 μg of ethidium bromide $mL^{-1}$. Ten μL mPCR products were subjected to electrophoresis for 100 min at 85V. Amplified bands were visualized and photographed under UV illumination. Bands present on the gels were compared to the banding pattern of standards from the American Type Culture Collection (ATCC) for *C. perfringens* toxigenic types A (ATCC13 containing a toxin and enterotoxin genes), B (ATCC3626 containing α, β, and ϵ toxin), C (ATCC13124 containing α and β toxin), and E (ATCC27324 containing α and τ toxin); bands were also compared to a 100 bp molecular weight standard (Bio-Rad).

Molecular Fingerprinting Analysis on Isolated *C. perfringens* Colonies:

Determination of the total number of *C. perfringens* strains (strain richness) was accomplished via randomly amplified polymorphic DNA (RAPD) PCR analysis. RAPD PCR genetic fingerprinting is a technique that detects and amplifies genomic polymorphisms using short arbitrary primers to generate reproducible strain-specific fingerprints (Williams et al., 1990). Often used in examination of strain diversity for a variety of different bacterial species, RAPD analysis has been effective in detecting diversity in microorganisms in clinical outbreaks (Power, 1996). The RAPD PCR analysis was performed using RAPD beads (GE, Buckinghamshire, UK), one 10mer primer, GGTGCGGGAA, and a thermal cycler (AB GeneAmp PCR System 2700). Each 25 μL PCR reaction contained 16 μL twice sterilized water, 5 μL primer, 4 μL template DNA, and one RAPD bead. Thermal cycler conditions were: 4 min at 94° C. followed by 45 cycles of 1 min at 94° C., 1 min at 36° C., and 2 min at 72° C. RAPD PCR products were separated via electrophoresis (PowerPac Basic, Bio-Rad) in 1% (w/v) agarose gels (Bio-Rad, Hercules, Calif.) with 0.5 pig of ethidium bromide $mL^{-1}$. Eight μL mPCR products were subjected to electrophoresis for 90 min at 85V. Amplified bands were visualized and photographed under UV illumination. The gels were processed, and DNA fingerprints were analyzed using Bio-Numerics (Applied Maths, Sint-Martens-Latum, Belgium). Strain richness was assessed at 80% similarity using the Pearson similarity coefficient with the unweighted pair group method using arithmetic averages (UPGMA).

Results:

Calf Scouring and Treatment Assignment:

As shown in Table 4, calves were assigned to a treatment group on an every other calf basis as they scoured. On day 3, there were 3 calves each in the electrolyte and the electrolyte+DFM groups, with the majority of the calves in the Control group. By day 42, 78% of the calves had scoured and were equally distributed across the electrolyte and electrolyte+DFM groups. Only 13 calves never scoured by day 42.

Fecal Microbial Shedding Evaluation:

On d 1, the majority of presumptive C. perfringens identified by selective plating did not contain the *C. perfringens* α toxin gene, indicting that they were not *C. perfringens*; whereas, on all other sampling dates, the majority of presumptive *C. perfringens* contained the α toxin genes indicating that they were *C. perfringens* Type A. A treatment x day interaction (P≦0.05) was observed for presumptive *C. perfringens* fecal shedding as determined by selective plate counts (FIG. 2). In the baseline samples (d 1), more (P≦0.05) presumptive *C. perfringens* were detected in the calves that were supplemented with electrolyte+DFM than in calves that were supplemented with electrolyte with calves that would not scour showing intermediate levels. On d 7, more (P≦0.05) presumptive *C. perfringens* was detected in electrolyte treated calves than in electrolyte+DFM treated and non-scouring calves. No differences between treatments were detected for confirmed *C. perfringens* Type A. This data would suggest that supplementation with the DFM decreased the *C. perfringens* Type A populations below that of the electrolyte only treatments by day 7, despite calves being significantly higher initially.

TABLE 4

Distribution of calves at each sampling day. Calves were either never treated for scours (non-scouring), treated with electrolyte therapy for scours, or treated with the electrolyte therapy containing a *Bacillus*-based direct fed microbial.

| Post-Placement | Non-Scouring | Electrolyte | Electrolyte + DFM | Total |
|---|---|---|---|---|
| d 3 | 59 | 3 | 3 | 65 |
| d 7 | 26 | 18 | 18 | 62 |
| d 14 | 14 | 24 | 23 | 61 |
| d 21 | 14 | 24 | 23 | 61 |
| d 28 | 13 | 24 | 24 | 61 |
| d 42 | 13 | 24 | 24 | 61 |

Example 4

Summary:

Supplementation of a commercial electrolyte product with a *Bacillus*-based direct-fed microbial (DFM) at the onset of scours increased gain, reduced *C. perfringens* fecal shedding, reduced therapeutic medication expenditures, and enhanced immune development in dairy calves. Scours promoted the development of a more mature immune system; however, supplementation with the DFM seemed to further enhance development of the T cell repertoire later in the study. The DFM also alleviated the inflammation from scours earlier than with electrolyte alone; however, both electrolyte treatments decreased inflammatory cell populations later in the study, allowing more energy for growth at this time point. Finally, the DFM altered immune cell populations in scouring calves to resemble those of non-scouring calves. This immunomodulation coincided with a decrease in *C. perfringens* fecal shedding in scouring calves during week one to concentrations similar to those witnessed in the feces of non-scouring calves. These results indicate that the immunomodulatory effects of the DFM and the reduction in *C. perfringens* via the DFM resulted in the calves appearing immunologically similar to the non-scouring calves, suggesting supplementation with the DFM resolved the *C. perfringens* challenge in scouring calves more quickly that calves provided only electrolyte therapy. Providing this DFM as a supplement to electrolyte therapy was an acceptable therapeutic treatment for scours as evidenced by a reduction in *C. perfringens*, increased gain, reduced medication cost, and quiescence of inflammatory responses along with stimulation of immune system leading to maturation.

Material and Methods:

The animals and treatments in this Example are the same as in Example 3 above.

Evaluation of Immune Development and Function:

Blood Collection:

A 20 mL blood sample was obtained by vena cava puncture from calves in each treatment and collected into tubes containing EDTA (BD Vacutainer, Preanalytical Solutions, Franklin Lakes, N.J.) on d 1, 3, 7, 14, 21, 28, and 42 post-placement for the isolation of peripheral blood mononuclear cells. An additional 5-10 mL blood sample was obtained and serum was collected for analysis of acute phase protein concentration and of immunoglobulin G (IgG) concentration from the serum samples collected on d 1 to determine passive transfer of antibody. Initially, at the time of placement, blood samples were obtained from 24 non-scouring calves. Following initial placement, samples from eight calves per treatment (scouring calves treated with electrolyte+DFM, scouring calves treated with electrolyte, and calves with no incidence of scouring) were obtained for a total of 24 calves on each sampling day. An attempt was made to sample eight calves in each treatment from the initial pool of 24 calves on each sampling day after scours were detected. If eight scouring calves from each electrolyte treatment were not available from the 24 calves initially sampled, samples were obtained from other scouring calves; however, the eight negative control calves (no incidence of scours) continued to be selected from the original pool of 24 non-scouring calves. If there were not enough calves scouring to make a total of eight calves per electrolyte treatment early in the trial then samples were taken from as many of those calves representing each treatment as possible. Calves were added to treatments on subsequent sampling days until eight calves represented each treatment. These calves continued to be sampled throughout the duration of the experiment.

Acute Phase Protein and Immunoglobulin G Analysis:

Blood serum was analyzed for concentration of the acute phase protein, $\alpha_1$-acid glycoprotein (AGP), and transfer of passive immunity (IgG) by radial immunodiffusion using diagnostic test kits (Cardiotech Services, Inc., Louisville, Ky.) according to the manufacturer's instructions.

Isolation of Peripheral Blood Mononuclear Cells:

Peripheral blood mononuclear cells were isolated by gradient centrifugation using Ficoll gradient (Histopaque 1077, density=1.077 g/mL; Sigma Chemical Co., St. Louis, Mo.). The blood was diluted in 15 mL phosphate buffered saline (PBS) and then overlaid onto Histopaque. The tubes were centrifuged at 400×g for 40 min at 10° C. The buffy layer containing the desired cells was removed and diluted in supplemented Roswell Park Memorial Institute medium (RPMI Complete; Sigma Chemical Co.; RPMI containing 1% penicillin-streptomycin, 1% L-glutamine, 5% fetal bovine serum). The cells were washed by centrifugation at 200×g for 10 min at 10° C. Cell concentration was determined by counting cells on a hemacytometer and cell viability was assessed using Trypan Blue exclusion dye (Sigma Chemical Co.). The cell concentration of each sample was adjusted to $5\times10^6$ cells/mL for flow cytometric analysis.

Flow Cytometric Analysis of Blood Immune Cell Populations:

A portion of the peripheral blood mononuclear cells were analyzed on a BD FACSCalibur flow cytometer (BD Biosciences, San Jose, Calif.) and CellQuest Pro software (BD Biosciences) using a panel of fluorescently labeled monoclonal antibodies to identify specific cell surface markers. Monoclonal antibodies and their specificities are illustrated in Table 5 below. Cells were stained using single monoclonal antibodies as well as double stained by combining two monoclonal antibodies to further differentiate cell populations important in the development of adaptive and innate immunity. Unlabeled cells were used as controls. All antibodies were unconjugated; as a result, fluorescein isothiocyanate (FITC, goat anti-mouse, IgG, Sigma Chemical Co.) and R-phycoerythrin (PE, goat anti-mouse IgG, Sigma Chemical Co.) were used to identify all monoclonal antibodies.

TABLE 5

Monoclonal antibodies specific for cattle leukocytes used to define cell surface molecule expression and differential populations of leukocytes derived from peripheral blood mononuclear cell population by flow cytometric analysis.

| Monoclonal Antibodies[a] | Clone* | Isotype | Specificity |
|---|---|---|---|
| CD4 | GC50A1 | IgM | CD4+ T helper cells |
| CD8α | CACT80C | IgG1 | CD8+ cytotoxic T cells; either αβ or γδ; also expressed on NK cells (natural killer cells) |
| CD14 | MM61A | IgG1 | LPS receptor on monocytes/macrophages |
| CD25 | LCTB2A | IgG3 | Interleukin-2 receptor; activated lymphocytes (B and T cells), and present on monocytes |
| CD45RO | GC44A | IgG3 | Memory T cells, a subset of B cells, monocytes |
| CD172a (SWC3) | DH59B | IgG1 | Monocytes, granulocytes, SWC3 equivalent in cattle |
| TCR1-N12 | CACT61A | IgM | γδ T cell receptor |
| Activation Molecule 2 | CACT77A | IgM | Activated γδ T cells |

[a]Monoclonal antibodies are mouse anti-bovine.
*Purchased from Veterinary Medical Research & Development, Inc., Pullman, WA.

Cell suspensions were added in 50 μL aliquots to the wells of a 96-well plate for staining. Monoclonal antibodies were diluted in PBS+ (PBS containing 1% bovine serum albumin and 0.1% sodium azide). Primary antibodies were administered in 50 μL aliquots into appropriate wells of the plate. The plates were incubated at 4° C. for 30 min. Following the cold incubation, excess antibody was washed away with two washings which consisted of the addition of 150 μL PBS+ to all wells containing cells, centrifuging the plates at 250×g for 4 min at 4° C., and discarding the supernatant. After the washings, 50₄ secondary antibody was added to appropriate wells. The plates were incubated at room temperature for 20 min. Following the room temperature incubation, the washing procedure was repeated. The staining procedure was repeated as appropriate to double stain the cells with the second primary antibody. Once the staining procedure was completed, 250 μL PBS+ was added to the wells containing cells, and cells were then transferred to BD Falcon tubes (Fisher Scientific, Waltham, Mass.) and acquired on the flow cytometer.

After acquisition of samples, populations were gated using the single stained cell surface markers for monocytes, CD45, CD3, and the unlabeled population. Regions were set around these four populations (R1 to R4, respectively). Multi-color gating was set on the forward scatter/side scatter (FSC/SSC) plots. One region (R5) was then drawn around the monocyte and CD3 population on the FSC/SSC plots. Another region (R6) was drawn around the CD45 population on the FSC/SSC plots. These two regions (R5 and R6) were combined as one gate. This gate was then applied to the fluorescent plots and used throughout the analysis on CellQuest Pro.

Macrophage Phagocytosis Assay:

The remaining portion of the peripheral blood mononuclear cells not used for flow cytometric analysis were plated in six-well plates containing glass coverslips for the isolation of monocyte-derived macrophages for the evaluation of phagocytic function. Briefly, cell suspensions were diluted to approximately $5 \times 10^6$ cells/mL in LM Hahn (Leibovitz's L-15/McCoy's Hahn media, Atlanta Biologicals, Lawrenceville, Ga.) medium. A glass coverslip was added to each well of a 6-well plate, and 2 mL of cell suspension was added to each well in duplicate for each sample. Each coverslip was completely covered by cell suspension. Cells were incubated overnight at 39.0° C. and 5% $CO_2$. Following this incubation, medium from each well was removed and was replaced by 2 mL of fresh LM Hahn medium warmed to 39.2° C. Cell cultures were incubated for an additional 5 h. Following the 5 h incubation, plates were removed from the incubator, excess medium was removed from each well, and 2 mL of a 4% porcine red blood cell (PRBC) suspension was added to each well. Plates were incubated with PRBC for 3 hours, after which coverslips were removed and non-adherent cells and excess PRBC were washed from the coverslip by rinsing with LM Hahn medium warmed to 39.2° C. Coverslips were then stained using the Hema 3 cell staining kit (Fischer Scientific), and percentage of phagocytic monocyte-derived macrophages and the average number of PRBC consumed by each phagocytic monocyte-derived macrophage was determined.

Statistical Analysis:

Analysis of variance was performed using the GLM and the mixed procedure of SAS (SAS Institute, Inc., Cary, N.C.). The model included the effects of sampling day, *Bacillus* supplementation, and appropriate interactions. Performance data was analyzed using the treatment designations at each week so that initially all calves were grouped as negative controls and at subsequent weigh-ins each week calves were placed into the appropriate treatment (similar to the analyses of microbial and immune data). Performance data was also analyzed by projecting the treatment designation of each calf at the end of the trial for all weeks so that initially all calves were assigned to their final treatment status. Differences between treatments were regarded as statistically significant at $P \leq 0.05$. Differences at $P \leq 0.10$ were considered tendencies.

Results:

Immune Measurements and Flow Cytometric Analysis:

Peripheral blood mononuclear cells were isolated from blood and a battery of monoclonal antibodies to specific cell surface molecules present on immune cells was utilized for flow cytometric analysis to identify immune cell populations and activation states. Cell isolation methods and laboratory procedures have been previously published in the scientific literature (Davis et al., 2004; Wistuba et al., 2005). Antibody panels used to define immune cell subsets for flow cytometric analyses are displayed above in Table 5. Differences in immune development between non-scouring calves and their scouring counterparts treated with either an electrolyte drench or the same drench with the DFM was evident based on differences in γδ T cell populations, T cell activation states, and induction of lymphocyte memory subsets that have been defined previously in cattle (Bembridge et. al. 1995). Specifically, a greater percentage of activated (CD25) and memory (CD45R0) T cell populations were present in the peripheral blood of scouring calves provided with an electrolyte drench containing the DFM compared to scouring calves treated with only an electrolyte drench and non-scouring calves (Table 6).

Activated (AM-2) populations of T cells expressing the γδ T cell receptor (TCR1) were also enhanced in those calves treated with the electrolyte drench containing the DFM compared to the other groups of calves. These data illustrate how the administration of different treatment regimens during a scouring challenge alters immune development in calves.

TABLE 6

Interleukin-2 receptor (IL-2R) expression within the CD4- and CD8-defined T cell subpopulations (as indicated by the presence of CD25 on the cell surface) of peripheral blood mononuclear cells isolated from dairy calves that were never treated for scours (Negative Control), treated with electrolyte therapy for scours, or treated with the electrolyte therapy containing a *Bacillus*-based DFM. (Main Effect Means)[§]

| T cell subsets (Double stain) | Negative Control | Electrolyte | Electro + DFM | SE* | P= |
|---|---|---|---|---|---|
| CD8$^-$CD25$^+$ | 13.73$^b$ | 13.23$^b$ | 16.59$^a$ | 1.00 | 0.03 |
| CD8$^-$CD45RO$^+$ | 20.59$^b$ | 19.51$^b$ | 24.92$^a$ | 1.58 | 0.03 |
| CD8$^-$TCR1$^+$ | 15.40$^b$ | 13.74$^b$ | 19.03$^a$ | 0.93 | 0.003 |
| TCR1$^+$AM-2$^+$ | 29.79$^a$ | 28.80$^b$ | 33.16$^a$ | 1.41 | 0.06 |

[§]Overall effect for combined samples at 3, 7, 21, 28, and 42 days post-placement.
*Due to unequal samples sizes between the three treatments, standard errors differed. The highest standard error from the three treatments is reported in the table.
$^{a,b}$Means without common superscripts are significantly different (P ≤ 0.05).

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

The invention is not intended to be limited to the preferred embodiments described above, but rather is intended to be limited only by the claims set out below. Thus, the invention encompasses all alternate embodiments that fall literally or equivalently within the scope of these claims.

BIBLIOGRAPHY

Abe, F., N. Ishibashi, and S. Shimamura. 1995. Effect of administration of Bifidobacteria and lactic acid bacteria to newborn calves and piglets. J. Dairy Sci. 78:2838-2846.

Baker, A. Davis, E., Rosener, D., Novak, K. White, R., Veldkamp, A., Rehberger, T. 2007. Development of a *Bacillus subtilis* product for a large commercial swine farm to reduce *Clostridium perfringens* and *Clostridium difficile* in neonatal pigs. J Anim Sci. 85(Suppl 1):102.

Bembridge, G. P., N. D. MacHugh, D. McKeever, E. Awino, P. Sopp, R. A. Collins, K. I. Gelder, and C. J. Howard. 1995. CD45RO expression on bovine T cells: relation to biological function. Immunology. 86:537-544.

Billington, S. J., E. U. Wieckowski, M. R. Sarker, D. Bueschel, J. G. Songer, and B. A. McClane. 1998. *Clostridium perfringens* Type E animal enteritis isolates with highly conserved, silent enterotoxin gene sequences. Infect. Immun. 66(9):4531-4536.

Cruywagen, C. W., I. Jordaan, and L. Venter. 1996. Effect of *Lactobacillus acidophilus* supplementation of milk replacer on preweaning performance of calves. J. Dairy Sci. 79:483-486.

Davis, M. E., C. V. Maxwell, G. F. Ed, D. C. Brown, and T. J. Wistuba. 2004. Dietary supplementation with phosphorylated mannans improves growth response and modulates immune function in weanling pigs. J. Anim. Sci. 82:1882-1891.

Donovan, D. C. 2002. Growth and health of Holstein calves fed milk replacers supplemented with antibiotics or enteroguard. J. Dairy Sci. 85:947-950.

Gebert, S., Kromm, C., Rehberger, T. 2006. Development of a direct-fed microbial to control pathogens associated with turkey poult production. Poult. Sci. 85(Suppl 1):71.

Gebert, S., Kromm, C. Rehberger, T. 2007. Effect of a *Bacillus*-based direct-fed microbial on turkey poult performance and changes within the gastrointestinal microflora. J. Anim. Sci. 85(Suppl 1):249.

Hatheway, C. L. 1990. Toxigenic *Clostridia*. Clinical Microbiology Reviews 3(1):66-98.

Hong, H. A., L. H. Duc, and S. M. Cutting. 2005. The use of bacterial spore formers as probiotics. FEMS Microbiol. Rev. 29:813-835.

Jenny, B. F., H. J. Vandijk, and J. A. Collins. 1991. Performance and fecal flora of calves fed a *Bacillus subtilis* concentrate. J. Dairy Sci, 74:1968-1973.

Jost, B. H., S. J. Billington, H. T. Trinh, D. M. Bueschel, and J. G. Songer. 2005. Atypical cpb2 genes, encoding beta2-toxin in *Clostridium perfringens* isolates of nonporcine origin. Infect. Immun. 73:652-656.

La Ragione, R. M., G. Casula, S. M. Cutting, and M. J. Woodward. 2001. *Bacillus subtilis* spores competitively exclude *Escherichia coli* O78:K80 in poultry. Vet. Microbiol. 79:133-142.

La Ragione, R. M. and M. J. Woodward. 2003. Competitive exclusion by *Bacillus subtilis* spores of *Salmonella enterica* serotype Enteritidis and *Clostridium perfringens* in young chickens. Vet. Microbiol. 94:245-256.

McDonough, S. P. 1994. Enteric pathogens in intensively reared veal calves. Am. J. Vet. Res. 55(11):1516-1520.

Morrill, J. L., J. M. Morrill, and A. M. Feyerherm. 1995. Plasma proteins and a probiotic as ingredients in milk replacer. J. Dairy Sci. 78:902-907.

Niilo, L. 1980. *Clostridium perfringens* in animal disease: a review of current knowledge. Can. Vet. J. 21:141-148.

Power, E. G. 1996. RAPD typing in microbiology—a technical review. J. Hosp. Infect. 34(4):247-265.

Songer, J. G. 1996. Clostridial enteric diseases of domestic animals. Clinical Microbiology Reviews 9(2):216-234.

Tam, N. K. M., N. Q. Uyen, H. A. Hong, L. H. Duc, T. T. Hoa, C. R. Serra, A. O. Henriques, and S. M. Cutting. 2006. The intestinal life cycle of *Bacillus subtilis* and close relatives. J. Bacteriol. 188:2692-2700.

Timmerman, H. M., L. Mulder, H. Everts, D. C. van Espen, E. van der Wal, G. Klaassen, S. M. G. Rouwers, R. Hartemink, F. M. Rombouts, and A. C. Beynen. 2005. Health and growth of veal calves fed milk replacers with or without probiotics. J. Dairy Sci. 88:2154-2165.

Vance, H. N. 1967. A survey of the alimentary tract of cattle for *Clostridium perfringens*. Can. J. Comp. Med. Vet. Sci. 31:260-264.

Williams, J. G., A. R. Kubelik, K. J. Livak, J. A. Rafalski, and S. V. Tingey. 1990. DNA polymorphisms amplified by arbitrary primers are useful as genetic markers. Nucleic Acids Res. 18:6531-6535.

Wistuba, T. J., E. B. Kegley, J. K. Apple, and M. E. Davis. 2005. Influence of fish oil supplementation on growth and immune system characteristics of cattle. J. Anim. Sci. 83:1097-1101.

Wu, X. Y., M. Walker, B. Vanselow, R. L. Chao, and J. Chin. 2006. Characterization of mesophilic bacilli in feces of feedlot cattle. J. Appl. Microbiol. 102:872-879.

What is claimed is:

1. A method comprising administering an effective amount of a composition comprising *Bacillus subtilis* strains 3A-P4

ATCC Accession No. PTA-6506, 22C-P1 ATCC Accession No. PTA-6508, and LSSA01 NRRL Accession No. NRRL B-50104 to a calf.

2. The method of claim 1, wherein the composition is administered with a milk replacer at a rate of about $2\times10^9$ CFU/calf/day, the CFU being a total microbial count of all of the *Bacillus subtilis* strains.

3. The method of claim 1, wherein the composition is administered with an electrolyte solution at a rate of about $3\times10^9$ CFU/dose, the CFU being a total microbial count of all of the *Bacillus subtilis* strains.

4. The method of claim 3, wherein the composition is administered until the calf is no longer scouring or until dehydration in the calf no longer persists.

5. The method of claim 1, wherein, when compared to calves not administered the composition, administration of the composition to the calf provides at least one of controlling pathogens in the calf and controlling scours in the calf.

6. The method of claim 1, wherein administration of the composition improves weight gain of the calf when compared to calves not administered the composition.

7. The method of claim 1, wherein administration of the composition inhibits at least one of *Clostridium, E. coli*, and *Salmonella* pathogens in the calf when compared to calves not administered the composition.

8. The method of claim 7, wherein the pathogens are *Clostridium* pathogens.

9. The method of claim 8, wherein the pathogens are *C. perfringens* type A pathogens.

10. The method of claim 1, wherein administration of the composition reduces treatments in the calf when compared to calves not administered the composition.

11. The method of claim 1, wherein administration of the composition reduces total treatment expenditures for the calf when compared to calves not administered the composition.

12. The method of claim 1, wherein administration of the composition reduces fecal shedding of presumptive *Clostridium* in the calf when compared to calves not administered the composition.

13. The method of claim 1, wherein administration of the composition enhances immune development in the calf when compared to calves not administered the composition.

14. The method of claim 1, wherein, when compared to calves not administered the composition, administration of the composition provides at least one of increasing weight gain in the calf and reducing injectible treatment expenditures.

15. The method of claim 1, further comprising modifying the *Bacillus* strains in the composition administered to the calf based on a change in pathogenic strains to which the calf is exposed.

16. The method of claim 1, wherein the composition is administered from birth.

17. The method of claim 1, wherein, when compared to calves not administered the composition, administration of the composition provides at least one of reducing presumptive *C. perfringens* shedding, increasing weight gain, reducing medication costs, reducing inflammatory response, and maturing the immune system by stimulating the immune system.

18. A method of providing a benefit to a calf, the method comprising:
orally administering an effective amount of a composition comprising *Bacillus subtilis* strains 3A-P4 ATCC Accession No. PTA-6506, 22C-P1 ATCC Accession No. PTA-6508, and LSSA01 NRRL Accession No. NRRL B-50104 to the calf,
wherein the benefit is selected from at least one of increased weight gain and decreased injectible treatment expenditures when compared to calves not administered the composition, and
wherein the composition is administered with a milk replacer at a rate of about $2\times10^9$ CFU/calf/day, the CFU being a total microbial count of all of the *Bacillus subtilis* strains, thereby providing the benefit to the calf.

19. A method of providing a benefit to a calf, the method comprising:
orally administering an effective amount of a composition comprising *Bacillus subtilis* strains 3A-P4 ATCC Accession No. PTA-6506, 22C-P1 ATCC Accession No. PTA-6508, and LSSA01 NRRL Accession No. NRRL B-50104 to the calf,
wherein the benefit is selected from at least one of reducing presumptive *C. perfringens* shedding, increasing weight gain, reducing medication costs, reducing inflammatory response, and maturing the immune system by stimulating the immune system when compared to calves not administered the composition, and
wherein the composition is administered with an electrolyte solution at a rate of about $3\times10^9$ CFU/dose, the CFU being a total microbial count of all of the *Bacillus subtilis* strains, thereby providing the benefit to the calf.

* * * * *